| United States Patent [19] | [11] Patent Number: 4,797,402 |
| Dorsey | [45] Date of Patent: Jan. 10, 1989 |

[54] COOLING ANTI-ITCH SKIN PREPARATIONS

[76] Inventor: Kenneth E. Dorsey, 8821 Bluff Wood La., Fort Washington, Md. 20744

[21] Appl. No.: 56,692

[22] Filed: Jun. 2, 1987

[51] Int. Cl.$^4$ .................. A61K 31/56; A61K 9/06
[52] U.S. Cl. ................................ 514/171; 514/919
[58] Field of Search ........................ 514/167–182

[56] References Cited

U.S. PATENT DOCUMENTS

| | | | |
|---|---|---|---|
| 3,980,778 | 9/1976 | Ayer et al. | 514/180 |
| 4,018,918 | 4/1977 | Ayer et al. | 514/24 |
| 4,044,120 | 8/1977 | Rowsell et al. | 424/45 |
| 4,130,643 | 12/1978 | Smith | 514/171 |
| 4,296,104 | 10/1981 | Herschler | 424/153 |
| 4,307,717 | 12/1981 | Hymes et al. | 424/485 |
| 4,353,896 | 10/1982 | Levy | 514/171 |
| 4,455,146 | 6/1984 | Noda et al. | 424/448 |
| 4,474,753 | 10/1984 | Haslam et al. | 514/171 |
| 4,512,978 | 4/1985 | Inwood | 514/552 |
| 4,514,384 | 4/1985 | Gallina | 514/171 |
| 4,518,583 | 5/1985 | Gallina | 424/80 |
| 4,675,009 | 6/1987 | Hymes et al. | 424/449 |

OTHER PUBLICATIONS

Hosek, C.A. 102: 32260a (1985).
Wohlrab, C.A. 101: 97537u (1984).
Oita et al, C.A. 100: 180117h (1984).
Wohlrab, C.A. 97: 33563s (1982).
Oita et al, C.A. 93: 13800yf (1980).
Das Gupta, C.A. 88: 158361v (1978).
Stoia et al, C.A. 77: 168618w (1972).
Arctander, "Perfume & Flavor Materials of Natural Origin", (1960), Peppermint Oil, Mentha Arvensis Oil.
Arctander, Perfume & Flavor Chemicals I-II (1969), L-Menthol, D-Camphor.

*Primary Examiner*—Shep K. Rose
*Attorney, Agent, or Firm*—Jerome J. Norris

[57] ABSTRACT

Cooling, anti-itch skin preparations in a hydrophilic base, comprising an anti-inflammatory corticosteroid, peppermint oil and urea.

7 Claims, No Drawings

COOLING ANTI-ITCH SKIN PREPARATIONS

BACKGROUND OF THE INVENTION

The invention pertains to new and improved therapeutic compositions formed from hydrocortisone for use on the skin, and methods for its preparation.

Hydrocortisone is chemically known as 17-hydroxycorticosterone, and is a well defined adrenocortical steroid with a rapid onset of action. It is used therapeutically for a broad spectrum of pathologic conditions; however, there are restrictions on its use as a non-prescription medicine due to the fact that elevated blood levels of hydrocortisone can be achieved rapidly, and the further fact that it is irritable at high levels.

FIELD OF THE INVENTION

Hydrocortisone containing compositions have been topically applied in the form of creams, lotions, solutions, ointments, aerosol sprays and gels, to treat the sites of inflammatory skin conditions arising from eczema, dermatitis, rashes, cutaneous condidiosis, pruritus ani, pruritus vulvae and lichen simplex chronicus.

It is believed that the anti-inflammatory mechanism of action of hydrocortisone per se functions by: (1) controlling the rate of protein synthesis; and (2) reducing the amount of prostaglandin substrate available for the enzyme. It is also theorized that hydrocortisone reduces immune hypersensitivity by reducing the inflammatory response.

While the low level of hydrocortisone approved for non-prescription use has been effective as an anti-inflammatory agent when topically applied in certain skin disorders, it has not been sufficient to relieve itching associated with the disorder As a consequence, the affected person has a tendency to rub or scratch the effected area and cause further irritation or inflammation of the disorder.

SUMMARY OF THE INVENTION

One object of the invention is to provide non-prescription levels of hydrocortisone in a hydrophilic ointment base, which provides cooling and anti-itch characteristics when topically applied to the situs of skin disorders.

A further object of the invention is to provide nonprescription levels of hydrocortisone in a hydrophilic ointment base, to provide cooling and anti-itch characteristics when applied to skin disorders, without lessening or eliminating the anti-inflammatory effect.

A yet further object of the invention is to provide non-prescription levels of hydrocortisone in a hydrophilic ointment base, in order to enable a user topically applying the base to avoid scratching which is occasioned by the itching associated with skin disorders, and facilitate faster healing.

In accordance with the present invention, symptoms from inflammatory skin conditions of eczema, dermatitis, rashes, and itching caused therefrom are prevented by periodic topical application to the skin area to be protected or treated of an effective amount of non-prescription levels of hydrocortisone in a hydrophilic ointment base together with minor amounts of peppermint oil and urea.

Relief is also provided for symptoms of irritated conditions of the skin, i.e. inflammation and redness due to soaps, detergents, cosmetics, jewelry, poison ivy, poison oak, sumac and insect bites.

The foregoing and other objects and provisions of the invention will become more apparent form the description hereinafter set forth.

DETAILED DESCRIPTION OF THE INVENTION

While corticosteroids, inclusive of hydrocortisone, have been prepared for topical applications in creams, lotions, solutions, ointments, aerosol sprays and gels, it is the ointments that have been received least acceptance, despite their beneficial therapeutic affect of skin lesion occlusiveness.

These ointment bases have been greasy and hydrophobic or water insoluble, and, as such, are difficult to wash off the skin.

However, it is a discovery of the present invention that non-prescription amounts of hydrocortisone can be used in a hydrophilic water miscible ointment base together with the addition of minor amounts of peppermint oil and urea to provide concomitant cooling and non-itching characteristics along with the anti-inflammatory effects of the hydrocortisone. The accompanying cooling and anti-itch characteristics enables a user topically applying the ointment base to avoid scratching which is occasioned by the itching associated with skin disorders, and thereby facilitate or promote faster healing of the lesions.

Hydrophilic ointments which are useful in the compositions of the invention are represented by the following general formulation:

| Ingredients | Percent by weight |
| --- | --- |
| Hydrocortisone | 0.1 to 0.5% |
| Peppermint Oil | 0.01 to 0.050% |
| Urea | 5.0 to 10.00% |
| Surfactant | 0.1 to 5.00% |
| Solvent | 1.0 to 20.00% |
| White Petrolatum | balance to 100.00% |

The ointment is prepared by heating the white petrolatum in a suitable stainless steel or glass-lined vessel until it is fluid and adding the active ingredients in the form of: (A) a suspension, in a finely powdered micronized state, or (B) solubilized in a solvent system comprising solvents such as propylene glycol, polyethylene glycol 300, polyethylene glycol 400 or polyethylene glycol 1540 alone or in combination with 1,2,6-hexanetriol, propylene carbonate or other such solvents; with the anti-inflammatory agent or hydrocortisone solubilized. Suitable oil soluble surfactants, such as, hydroxylated lanolin, ethoxylated lanolin derivatives or polyoxyethylene esters can be added into the petrolatum to make the ointment water miscible.

In the preferred embodiment of the invention, the anti-inflammatory steriod will be hydrocortisone, and it may be present in amounts from about 0.1 to 0.5% by weight of the hydrophilic composition mix.

The preferred amounts of peppermint oil may be present in amounts from about 0.01 to 0.050% by weight each, based on the weight of the hydrophilic composition mix.

Urea may be present in the preferred amounts of from about 5.0 to about 10.0% by weight based on the hydrophilic composition ointment mix.

Moreover, while hydrocortisone is the preferred topically active anti-inflammatory corticosteroid, any topically active anti-inflammatory corticosteroid will suffice in the context of the invention, as it is widely understood that all of these generally function through the mechanism of: controlling the rate of protein synthesis; reducing the amount of prostaglandin substrate available for the enzyme; and reducing immune hypersensitivity by reducing the inflammatory response. However, hydrocortisone and its lower esters and mixtures thereof are most preferred.

The general method of treatment is effected by applying the ointment to the situs of the affected area from one to about four times per day or about 21 times per week until the inflammation is relieved.

EXAMPLE 1

| Ingredients | Parts by weight |
| --- | --- |
| Hydrocortisone | 0.50 |
| Peppermint Oil | 0.025 |
| Urea | 10.00 |
| Hydroxylated Lanolin | 5.00 |
| Propylene Glycol | 10.00 |
| White Petrolatum | 74.48 |

EXAMPLE 2

| Ingredients | Parts by weight |
| --- | --- |
| Hydrocortisone acetate | 0.1 |
| Peppermint Oil | 0.040 |
| Urea | 5.00 |
| Ethoxylated Lanolin | 2.50 |
| Polyethylene Glycol 300 | 5.00 |
| White Petrolatum | 87.38 |

EXAMPLE 3

| Ingredients | Parts by weight |
| --- | --- |
| Hydrocortisone butyrate | 0.25 |
| Peppermint Oil | 0.050 |
| Urea | 7.50 |
| Polythylene glycol 400 | 1.00 |
| White Petrolatum | 91.26 |

A small amount of the ointment of Example 1 is applied at the site of inflammation on 20 patients having eczematous dermatitis from 1 to 4 times a day for seven days. In addition to the inflammation being hydrocortizone responsive, all patients indicated experiencing a cooling effect in the area of inflammation and the absence of the itching tendency normally associated with the inflammation.

The same tests were performed with the ointment of Example 2 on 20 patients with seborrheic dermatitis, and the results obtained were the same as those in Example 1.

Small amounts of the ointment from Example 3 were used on 20 patients with contact dermatitis and the results obtained were the same as those in Examples 1 and 2.

Peppermint oil is an essential oil obtained by distilling peppermint or mentha piperita (dried leaves and flowering tops of mentha piperita).

While there is no desire to be bound by a theory of the manner in which peppermint oil augments the anti-inflammatory benefits of hydrocortisone, it is believed that the menthol naturally present in said peppermint relieves the itching by substituting or imposing a cooling sensation.

It is further theorized that peppermint camphor naturally present in said peppermint induces a mild antipruritic or anti-itch benefit through its anesthetic properties. It would therefore appear that some collaborative or synergistic effect from the two mentioned materials, naturally contained in the peppermint contribute to and augment the anti-inflammatory benefits of the hydrocortisone.

Urea provides a softening and moisturizing effect on the stratum corneum and thereby provides good theraphy for dry skin and the pruritis associated with it. In other words, in the context of the invention, it appears to have an antipruritic effect separate and apart from its hydration characteristics.

While the invention has been described by reference to preferred embodiments, it is to be understood that many variations and substitutions can be made in the context of hydrophilic ointment formulation without departing from the spirit and scope of the invention, which is defined by the appended claims.

What is claimed is:

1. A hydrophilic ointment petrolatum base composition for the topical adminstration of an antiflammatory corticosteroid which provides a cooling effect and anti-itching characterisitcs consisting essentially of:

an antiflammatory effective amount of a corticosteroid; peppermint oil in amounts of from about 0.01 to about 0.05% by weight; urea in amounts of from about 5.0 to about 10.0% by weight; and an oil soluble surfactant selected from hydroxylated lanolin, ethoxylated lanolin or polyoxyethylene esters, based on the weight of the composition.

2. The composition of claim 1, wherein the corticosteroid is selected from the group consisting of hydrocortisone, hydrocortisone acetate, hydrocortisone butyrate, hydrocortisone valerate and mixtures thereof.

3. The composition of claim 1, wherein the corticosteroid is in suspension in a finely powdered micronized state.

4. The composition of claim 1, wherein the corticosteroid is solubilized in a solvent.

5. The composition of claim 3, wherein the corticosteroid is selected from the group consisting of hydrocortisone, hydrocortisone acetate, hydrocortisone butyrate, hydrocortisone valerate and mixtures thereof.

6. The composition of claim 4, wherein the corticosteroid is selected from the group consisting of hydrocortisone, hydrocortisone acetate, hydrocortisone butyrate, hydrocortisone valerate and mixtures thereof.

7. The composition of claim 4, wherein the solvent is selected from the group consisting of propylene glycol, polyethylene glycol 300, polyethylene glycol 400 or polyethylene glycol 1540 alone or in combination with 1, 2, 6-hexontriol or propylene carbonate.

* * * * *